United States Patent
Hogan, II et al.

(10) Patent No.: US 11,419,868 B2
(45) Date of Patent: Aug. 23, 2022

(54) LOW DOSE PRODUCT AND METHOD FOR TREATING DIARRHEA

(71) Applicant: MAREGADE RX, LLC, Jackson, MS (US)

(72) Inventors: Reed B. Hogan, II, Jackson, MS (US); Joseph A. Fix, Lawrence, KS (US)

(73) Assignee: White Sands Pharma LLC, Little Rock, AR (US)

( * ) Notice: Subject to any disclaimer, the term of this patent is extended or adjusted under 35 U.S.C. 154(b) by 0 days.

(21) Appl. No.: 16/513,342

(22) Filed: Jul. 16, 2019

(65) Prior Publication Data

US 2020/0108062 A1   Apr. 9, 2020

Related U.S. Application Data

(63) Continuation of application No. 15/853,586, filed on Dec. 22, 2017, now abandoned.

(60) Provisional application No. 62/438,726, filed on Dec. 23, 2016.

(51) Int. Cl.
| | |
|---|---|
| *A61K 31/495* | (2006.01) |
| *A61K 31/426* | (2006.01) |
| *A61K 31/341* | (2006.01) |
| *A61P 1/12* | (2006.01) |

(52) U.S. Cl.
CPC .......... *A61K 31/495* (2013.01); *A61K 31/341* (2013.01); *A61K 31/426* (2013.01); *A61P 1/12* (2018.01)

(58) Field of Classification Search
None
See application file for complete search history.

(56) References Cited

U.S. PATENT DOCUMENTS

| | | | |
|---|---|---|---|
| 5,204,118 | A | 4/1993 | Goldman et al. |
| 6,264,984 | B1 | 7/2001 | Hussein |
| 8,207,188 | B2 | 6/2012 | Nicolaou et al. |
| 8,207,292 | B2 | 6/2012 | Nicolaou et al. |
| 9,717,726 | B2 | 8/2017 | Hogan, II |
| 10,034,875 | B2 | 7/2018 | Hogan, II |
| 11,058,681 | B2 | 7/2021 | Hogan, II |
| 2004/0071773 | A1 | 4/2004 | Kajiyama |
| 2007/0254050 | A1 | 11/2007 | Quart |
| 2009/0042972 | A1 | 2/2009 | Rogowski |
| 2009/0312358 | A1 | 12/2009 | Siddiqi |
| 2010/0144718 | A1 | 6/2010 | Nicolaou et al. |
| 2011/0003781 | A1 | 1/2011 | Du |
| 2014/0275116 | A1* | 9/2014 | Hogan, II ............... A61P 1/12 514/255.04 |
| 2017/0049770 | A1 | 2/2017 | Hogan, II |
| 2018/0185356 | A1 | 7/2018 | Hogan, II |
| 2019/0038619 | A1 | 2/2019 | Hogan, II |
| 2020/0108062 | A1 | 4/2020 | Hogan, II et al. |
| 2022/0047583 | A1 | 2/2022 | Hogan, II |

FOREIGN PATENT DOCUMENTS

| | | |
|---|---|---|
| EP | 1832287 | 12/2007 |
| WO | 1995/01792 | 1/1995 |
| WO | 2002/43649 | 6/2002 |
| WO | 2006/041367 | 4/2006 |
| WO | 2008/128115 | 10/2008 |
| WO | 2014/152420 | 9/2014 |
| WO | 2018/119464 | 6/2018 |

OTHER PUBLICATIONS

Kharkevich, D.A., "Pharmacology", Geotar-media, chapter 15, pp. 371-377, (2008).
PEPCID® Prescribing Information, MERCK & Co., pp. 1-12, (2001).
Kuznik, E. et al., "Diabetic autonomic neuropathy of the gastrointestinal tract", Gastroenterology Review, vol. 15, No. 2, pp. 89-93, (2020).
Web Page: "Cetirizine side effects", Drugs.com, pp. 1-5, Product Information, obtained from: www.drugs.com/sfx/cetirizine-side-effects.html, printed on Feb. 20, 2020.
Web Page: "Zyrtec Tablets", Zyrtec.com, pp. 1-8, Product Information, obtained from: www.zyrtec.com/products/zyrtec-tablets, printed on Feb. 20, 2020.
Web Page: "Famotidine side effects", Drugs.com, pp. 1-6, Product Information, obtained from: www.drugs.com/sfx/famotidine-side-effects.html, printed on Feb. 20, 2020.
Web Page: "Pepcid Dosage", Drugs.com, pp. 1-3, Product Information, obtained from: www.drugs.com/dosage/pepcid.html, printed on Feb. 21, 2020.
Wald, A., "Treatment of irritable bowel syndrome in adults", UpToDate, pp. 1-19, obtained from: www.uptodate.com/contents/treatment-of-irritable-bowel-syndrome-in-adults?search=treatment%20of%20irritable%20bowel%20syndrome&source=search_result&selectedTitle=1~150&usage_type=default&display_rank=1, printed on Oct. 26, 2017.
Krishnamurthi, S.S. et al., "Management of acute chemotherapy-related diarrhea", UpToDate, pp. 1-27, obtained from: www.uptodate.com/contents/management-of-acute-chemotherapy-related-diarrhea?search=Management of acute chemotherapy-related diarrhea&source=search_result&selectedTitle=1~150&usage_type=default&display_rank=1, printed on Apr. 14, 2020.
Wilcox, C.M., "Evaluation of the HIV-infected patient with diarrhea", UpToDate, pp. 1-18, obtained from: www.uptodate.com/contents/search?search=Evaluation of the HIV-infected patient with diarrhea&sp=0&searchType=PLAIN_TEXT&source=USER_INPUT&searchControl=TOP_PULLDOWN&autoComplete=false, printed on Apr. 13, 2020.
LaRocque, R. et al., "Approach to the adult with acute diarrhea in resource-rich settings", UpToDate, pp. 1-18, obtained from: www.uptodate.com/contents/approach-to-the-adult-with-acute-diarrhea-in-resource-rich-settings?search=Approach to the adult with acute diarrhea in resource-rich settings&source=search_result&selectedTitle=1~150&usage_type=default&display_rank=1, printed on Apr. 13, 2020.

(Continued)

*Primary Examiner* — Craig D Ricci
(74) *Attorney, Agent, or Firm* — Evan Law Group LLC

(57) ABSTRACT

A method of treating diarrhea in a patient includes administering a dose of 2.0-7.0 mg of cetirizine and 3.0-15.0 mg of famotidine.

15 Claims, 8 Drawing Sheets

(56) References Cited

OTHER PUBLICATIONS

Mason, J.B., "Approach to the adult patient with suspected malabsorption", UpToDate, pp. 1-21, obtained from: www.uptodate.com/contents/approach-to-the-adult-patient-with-suspected-malabsorption, printed on Apr. 13, 2020.

Wald, A., "Pathophysiology of irritable bowel syndrome", UpToDate, pp. 1-13, obtained from: www.uptodate.com/contents/pathophysiology-of-irritable-bowel-syndrome?search=Pathophysiology of irritable bowel syndrome&source=search_result&selectedTitle=1~150&usage_type=default&display_rank=1, (2016).

U.S. Appl. No. 16/029,384, filed Jul. 6, 2018.

Schiller, L.R., "Secretory Diarrhea", Current Gastroenterology Reports, vol. 1, issue 5, pp. 389-397, (1999).

Schiller, L.R. et al., "Studies of the prevalence and significance of radiolabeled bile acid malabsorption in a group of patients with idiopathic chronic diarrhea", Gastroenterology, vol. 92, pp. 151-160, (1987).

Fordtran, J.S. et al., "Pathophysiology of chronic diarrhoea: insights derived from intestinal perfusion studies in 31 patients", Clinics in Gastroenterology, vol. 15, No. 3, pp. 477-490, (1986).

Lunardi, C. et al., "Double-blind cross-over trial of oral sodium cromoglycate in patients with irritable bowel syndrome due to food intolerance", Clinical & Experimental Allergy, vol. 21, issue 5, pp. 569-572, (1991).

Fine, K.D. et al., "AGA technical review on the evaluation and management of chronic diarrhea", Gastroenterology, vol. 116, issue 6, pp. 1464-1486, (1999).

O'Sullivan, M. et al., "Increased mast cells in the irritable bowel syndrome", Neurogastroenterology and Motility, vol. 12, pp. 449-457, (2000).

Spiller, R.C. et al., "Increased rectal mucosal enteroendocrine cells, T lymphocytes, and increased gut permeability following acute Campylobacter enteritis and in post-dysenteric irritable bowel syndrome", Gut, vol. 47, pp. 804-811, (2000).

Theoharides, T.C. et al., "Critical role of mast cells in inflammatory diseases and the effect of acute stress", Journal of Neuroimmunology, vol. 146, pp. 1-12, (2004).

Barbara, G. et al., "New pathophysiological mechanisms in irritable bowel syndrome", Alimentary Pharmacology & Therapeutics, vol. 20, supplement 2, pp. 1-9, (2004).

Dunlop, S.P. et al., "Abnormal intestinal permeability in subgroups of diarrhea-predominant irritable bowel syndromes", American Journal of Gastroenterology, vol. 101, No. 6, pp. 1288-1294, (2006).

Barbara, G. et al., "Functional gastrointestinal disorders and mast cells: implications for therapy", Neurogastroenterology and Motility, vol. 18, pp. 6-17, (2006).

Halvorson, H.A. et al., "Postinfectious irritable bowel syndrome—a meta-analysis", American Journal of Gastroenterology, vol. 101, pp. 1894-1899, (2006).

Posserud, I. et al., "Small intestinal bacterial overgrowth in patients with irritable bowel syndrome", Gut, vol. 56, pp. 802-808, (2007).

Lewis, J,T. et al., "Crystal-storing histiocytosis due to massive accumulation of charcot-leyden crystals: A unique association producing colonic polyposis in a 78-year-old woman with eosinophilic colitis", American Journal of Surgical Pathology, vol. 321, No. 3, pp. 481-485, (2007).

Jakate, S. et al., "Mastocytic enterocolitis increased mucosal mast cells in chronic intractable diarrhea", Archives of Pathology & Laboratory Medicine, vol. 130, pp. 362-367, (2006).

Kirsch, R.H. et al., "Histopathological alterations in irritable bowel syndrome", Modem Pathology, vol. 19, pp. 1638-1645, (2006).

Ramos, L. et al., "Stress-mast cell axis and regulation of gut mucosal inflammation: from intestinal health to an irritable bowel", Med Clin (Barc), vol. 129, No. 2, pp. 61-69, (2007) English Abstract.

Piche, T. et al., "Mast cells and cellularity of the colonic mucosa correlated with fatigue and depression in irritable bowel syndrome", Gut, vol. 57, pp. 468-473, (2008).

Visser, J. et al., "Tight junctions, intestinal permeability, and autoimmunity celiac disease and type 1 diabetes paradigms", Annals—New York Academy of Sciences, vol. 1165, pp. 195-205, (2009).

Walker, M.M. et al., "Duodenal mastocytosis, eosinophilia and intraepithelial lymphocytosis as possible disease markers in the irritable bowel syndrome and functional dyspepsia", Alimentary Pharmacology & Therapeutics, vol. 29, pp. 765-773, (2009).

Thabane, M. et al., "Post-infectious irritable bowel syndrome", World Journal of Gastroenterology, vol. 15, No. 29, pp. 3591-3596, (2009).

Walker, M.M. et al., "Implications of eosinophilia in the normal duodenal biopsy—an association with allergy and functional dyspepsia", Alimentary Pharmacology & Therapeutics, vol. 31, pp. 1229-1236, (2010).

Klooker, T.K. et al., "The mast cell stabiliser ketotifen decreases visceral hypersensitivity and improves intestinal symptoms in patients with irritable bowel syndrome", Gut, vol. 59, pp. 1213-1221, (2010).

Martinez, C. et al., "The jejunum of diarrhea-predominant irritable bowel syndrome shows molecular alterations in the tight junction signaling pathway that are associated with mucosal pathobiology and clinical manifestations", American Journal of Gastroenterology, vol. 107, pp. 736-746, (2012).

Smith, M.J. "IBS remains a mysterious disorder, with few effective remedies", Gastroenterology and Endoscopy News, vol. 63, No. 4, pp. 1-6, (2012).

Pyleris, E. et al., "The prevalence of overgrowth by aerobic bacteria in the small intestine by small bowel culture: relationship with irritable bowel syndrome", Digestive Diseases and Sciences, vol. 57, pp. 1321-1329, (2012).

Vivinus-Nebot, M. et al., "Combination of allergic factors can worsen diarrheic irritable bowel syndrome: role of barrier defects and mast cells", American Journal of Gastroenterology, vol. 107, pp. 75-81, (2012).

Akhavein, A. et al., "Allergic mastocytic gastroenteritis and colitis: an unexplained etiology in chronic abdominal pain and gastrointestinal dysmotility", Gastroenterology Research and Practice, pp. 1-6, (2012).

Martinez, C. et al., "Diarrhoea-predominant irritable bowel syndrome: an organic disorder with structural abnormalities in the jejunal epithelial barrier", Gut, vol. 62, issue 8, pp. 1160-1168, (2013).

Braak, B. et al., "Mucosal immune cell numbers and visceral sensitivity in patients with irritable bowel syndrome: is there any relationship?", American Journal of Gastroenterology, vol. 107, pp. 715-726, (2012).

Theoharides, T.C. et al., "Irritable bowel syndrome and the elusive mast cells", American Journal of Gastroenterology, vol. 107, No. 5, pp. 727-729, (2012).

Farhadi, A. et al., "Mucosal mast cells are pivotal elements in inflammatory bowel disease that connect the dots: stress, intestinal hyperpermeability and inflammation", World Journal of Gastroenterology, vol. 13, No. 22, pp. 3027-3030, (2007).

Juckett, G. et al., "Evaluation of chronic diarrhea", American Family Physician, vol. 84, No. 10, pp. 1119-1126, (2011).

"Diarrhea", National Digestive Diseases Information Clearinghouse, pp. 1-8, (2011).

Forbes, D.A. et al., "Laxative abuse and secretory diarrhoea", Archives of Disease in Childhood, vol. 60, No. 1, pp. 58-60, (1985).

DuPont, H.L. et al., "Diarrhea", National Digestive Diseases Information Clearinghouse, 8 pages, Jan. 2012.

Lever, D.S. et al., "Acute Diarrhea", Cleveland Clinic, Center for Continuing Education publications: Disease Management Project, pp. 1-8, (2010).

MedlinePlus, "H2 blockers", U.S. National Library of Medicine, National Institutes of Health, 3 pages, found at www.nlm.nih.gov/medlineplus/ency/patientinstructions/000382.htm, printed on Feb. 11, 2013.

Runge, J.W. et al., "Histamine antagonists in the treatment of acute allergic reactions" Annals of Emergency Medicine, vol. 21, No. 3, pp. 237-242, (1992).

(56) References Cited

OTHER PUBLICATIONS

Lin, R.Y. et al., "Improved outcomes in patients with acute allergic syndromes who are treated with combined $H_1$ and $H_2$ antagonists", Annals of Emergency Medicine, vol. 36, No. 5, pp. 462-468, (2000).
He, S. et al., "Formulation and evaluation of novel coated floating tablets of bergenin and cetirizine dihydrochloride for gastric delivery", Drug Development and Industrial Pharmacy, vol. 38, No. 10, pp. 1280-1288, (2012).
Akin, C. et al., "Mast cell activation syndrome: Proposed diagnostic criteria", Journal of Allergy and Clinical Immunology, vol. 126, No. 6, pp. 1099-1104, (2010).
Hamilton, M.J. et al., "Mast cell activation syndrome: A newly recognized disorder with systemic clinical manifestations", Journal of Allergy and Clinical Immunology, vol. 128, No. 1, pp. 147-152, (2011).
Valent, P., "Mast cell activation syndromes: definition and classification", Allergy, vol. 68, pp. 417-424, (2013).
Simons, F.E. et al., "Second-generation H1-receptor antagonists", Annals of Allergy, vol. 66, No. 1, pp. 5-16, (1991).
Melcescu, E. et al., "The various faces of autoimmune endocrinopathies: Non-tumoral hypergastrinemia in a patient with lymphocytic colitis and chronic autoimmune gastritis", Experimental and Molecular Pathology, vol. 93, Issue 3, pp. 434-440, (2012).
Elvevi, A., et al., "Severe chronic diarrhea and maculopapular rash: A case report", World Journal of Gastroenterology, vol. 17, issue 34, pp. 3948-3952, (2011).
Valent, P. et al., "Standards and standardization in mastocytosis: consensus statements on diagnostics, treatment recommendations and response criteria", European Journal of Clinical Investigation, vol. 37, No. 6, pp. 435-453, (2007).
"Mast cell" found at http://en.wikipedia.org/wiki/Mast_cell, 5 pages, (2014).
Boyce, P.M. et al., "Irritable bowel syndrome according to varying diagnostic criteria: are the new Rome II criteria unnecessarily restrictive for research and practice?", American Journal of Gastroenterology, vol. 95, issue 11, pp. 3176-3183, (2000).
Chey, W.D. et al., "Utility of the Rome I and Rome II criteria for irritable bowel syndrome in US women", American Journal of Gastroenterology, vol. 97, No. 11, pp. 2803-2811, (2002).
Barbara, G. et al., "Mast cell-dependent excitation of visceral-nociceptive sensory neurons in irritable bowel syndrome", Gastroenterology, vol. 132, issue 1, pp. 26-37, (2007).
Kushnir-Sukhov, N.M. et al., "Mastocytosis", Allergy and Allergic Diseases, Second Edition, pp. 1878-1893, (2009).
"How are mast cell issues treated?", Microscopic Colitis Support, 5 pages, found at www.microscopiccolitis.org/articles/How%20are%20mast%20cell%20issues%20treated.html, Apr. 6, 2013.
Stacpoole, P.W. et al., "Combination H1 and H2 receptor antagonist therapy in diabetic autonomic neuropathy", Southern Medical Journal, vol. 75, No. 5, pp. 634-635, (1982).
International Search Report dated Jun. 24, 2014, for PCT application No. PCT/US2014/027323, 9 pages.
Thonhofer, R. et al., "Mastocytic enterocolitis as a rare cause of chronic diarrhea in a patient with rheumatoid arthritls", Wiener klinische Wochenschrift, vol. 123, pp. 297-298, (2011).
Linde, R. et al., "Combination H1 and H2 receptor antagonist therapy in mastocytosis", Annals of Internal Medicine, vol. 92, No. 5, p. 716, (1980).
Lonnroth, I. et al., "Chlorpromazine reverses diarrhea in piglets caused by enterotoxigenic *Escherichia coli*", Infection and Immunity, vol. 24, No. 3, pp. 900-905, (1979).
Spiegel, D.R. et al., abstract of "Treatment of irritable bowel syndrome with comorbid anxiety symptoms with mirtazapine", Database Biosis, Biosciences Information Service, vol. 34, 2 pages, (2011).
Berry, E.M. et al., "Carcinoid myopathy and treatment with cyproheptadine (Periactin)", Gut, vol. 15, pp. 34-38, (1974).
Aly, A. et al., "Effect of an H2-receptor blocking agent on diarrhoeas after extensive small bowel resection in crohn's disease", Acta Medica Scandinavica, vol. 207, No. 1-2, pp. 119-122, (1980).

Fondacaro, J.D. et al., "Cecectomized rat—A model of experimental secretory diarrhea in conscious animals", Journal of Pharmacological Methods, vol. 24, pp. 59-71, (1990).
Rabbani, G.H., Abstract of "Mechanism and treatment of diarrhoea due to vibrio cholerae and *Escherichia coli*: roles of drugs and prostaglandins", Database Medline, 2 pages, (1996).
Qin, Z. et al., "Synergistic action of famotidine and chlorpheniramine on acetic acid-induced chronic gastric ulcer in rats", World Journal of Gastroenterology, vol. 11, No. 45, pp. 7203-7207, (2005).
Lorenz, W. et al., abstract of "Studies on the effectiveness of H1-+H2-antagonist combinations in preventing life-threatening anaphylactoid reactions in anaesthesia and surgery: Problems with selecting the animal model from clinical data and with "equi-effective" doses", Database Embase, 2 pages, (1992).
Sultana, N. et al., "In vitro studies of the interaction between cetirizine and H2 receptor antagonists using spectrophotometry and reversed-phase high-performance liquid chromatography", Medicinal Chemistry Research, vol. 19, pp. 462-474, (2010).
International Search Report dated Oct. 9, 2014, for PCT application No. PCT/US2014/027323, 22 pages.
"H2 blockers (acid reducers) for gastroesophageal reflux disease (GERD)", found at www.webmd.com/heartburn-gerd/h2-blockers-acid-reducers-for-gastroesophageal-reflux-disease-gerd, 2 pages, printed on Feb. 11, 2013.
Quigley, E. et al., "Irritable bowel syndrome: a global perspective", World Gastroenterology Organisation Global Guideline, pp. 1-20, (2009).
American Gastroenterological Association, "American Gastroenterological Association medical position statement: Guidelines for the evaluation and management of chronic diarrhea", Gastroenterology, vol. 116, pp. 1461-1463, (1999).
Del Cuvillo, A. et al., "Comparative pharmacology of the $H_1$ antihistamines", Journal of Investigational Allergology and Clinical Immunology, vol. 16, supplement 1, pp. 3-12, (2006).
Baker, E.H. et al., "Complications of laxative abuse", Annual Review of Medicine, vol. 47, pp. 127-134, (1996).
Arevalo, F. et al., "Increase of intraepithelial lymphocytes in patients with irritable bowel syndrome", Rev. Gastroenterology Peru, vol. 31, No. 4, pp. 315-318, (2011), English Abstract.
Bleehan, S.S. et al., "Cimetidine and chlorpheniramine in the treatment of chronic idiopathic urticaria: a multi-centre randomized double-blind study", British Journal of Dermatology, vol. 117, issue 1, pp. 81-88, (1987).
Demi, K-F., et al., "Interactions of histamine $H_1$-receptor agonists and antagonists with the human histamine $H_4$-receptor", Molecular Pharmacology, vol. 76, No. 5, pp. 1019-1030, (2009).
DeSilva, A.P. et al., "Subclinical mucosal inflammation in diarrhea-predominant irritable bowel syndrome (IBS) in a tropical setting", Scandinavian Journal of Gastroenterology, vol. 47, No. 6, pp. 619-624, (2012).
Dorsch, W., et al., "Histamine$_1$-histamine$_2$ antagonism: effect of combined clemastine and cimetidine pretreatment on allergen and histamine-induced reactions of the guinea pig lung in vivo and in vitro", Agents and Actions, vol. 12, issue 1-2, pp. 113-118, (1982).
Echizen, H., et al., "Clinical pharmacokinetics of famotidine", Clinical Pharmacokinetics, vol. 21, issue 3, pp. 178-194, (1991).
Flockhart, D.A. et al., "Selection of drugs to treat gastro-oesophageal reflux disease: the role of drug interactions", Clinical Pharmacokinetics, vol. 39, issue 4, pp. 295-309, (2000).
Fogel, W.A. et al., "Histamine in idiopathic inflammatory bowel diseases—not a standby player", Folia Medica Cracoviensia, vol. 46, No. 3-4, pp. 107-118, (2005).
Ford, A.C. et al., "Mucosal inflammation as a potential etiological factor in irritable bowel syndrome: a systematic review", Journal of Gastroenterology, vol. 46, No. 4, pp. 421-431, (2011).
Harvey, R.P. et al., "The effect of $H_1$ and $H_2$ blockade on cutaneous histamine response in man", The Journal of Allergy and Clinical Immunology, vol. 65, issue 2, pp. 136-139, (1980).
Hofstra, C.L. et al., "Histamine $H_4$ receptor mediates chemotaxis and calcium mobilization of mast cells", The Journal of Pharmacology and Experimental Therapeutics, vol. 305, No. 3, pp. 1212-1221, (2003).

(56) References Cited

OTHER PUBLICATIONS

Humphries, T.J. et al., "Review article: drug interactions with agents used to treat acid-related diseases", Alimentary Pharmacology & Therapeutics, vol. 13, supplement 3, pp. 18-26, (1999).
Irwin, R.B. et al., "Mediator release in local heat urticaria: protection with combined H1 and H2 antagonists", The Journal of Allergy and Clinical Immunology, vol. 76, issue 1, pp. 35-39, (1985).
Kristjansson, G. et al., "Clinical and subclinical intestinal inflammation assessed by the mucosal patch technique: studies of mucosal neutrophil and eosinophil activation in inflammatory bowel diseases and irritable bowel syndrome", Gut, vol. 53, pp. 1806-1812, (2004).
Lim, H.D. et al., "Evaluation of histamine $H_1$-, $H_2$-, and $H_3$-receptor ligands at the human histamine $H_4$ receptor: identification of 4-methylhistamine as the first potent and selective $H_4$ receptor agonist", The Journal of Pharmacology and Experimental Therapeutics, vol. 314, No. 3, pp. 1310-1321, (2005).
Ling, P. et al., "Histamine $H_4$ receptor mediates eosinophil chemotaxis with cell shape change and adhesion molecule upregulation", British Journal of Pharmacology, vol. 142, pp. 161-171, (2004).
Lippert, U. et al., "Human skin mast cells express H2 and H4, but not H3 receptors", The Journal of Investigative Dermatology, vol. 123, pp. 116-123, (2004).
Matsushita, A. et al., "Advantages of histamine H4 receptor antagonist usage with H1 receptor antagonist for the treatment of murine allergic contact dermatitis", Experimental Dermatology, vol. 21, pp. 710-720, (2012).
Moscati, R.M. et al., "Comparison of cimetidine and diphenhydramine in the treatment of acute urticaria", Annals of Emergency Medicine, vol. 19, issue 1, pp. 12-15, (1990).
Murch, S., "Allergy and intestinal dysmotility—evidence of genuine causal linkage?", Current Opinion in Gastroenterology, vol. 22, issue 6, pp. 664-668, (2006).
Ohsawa, Y. et al., "The antagonism of histamine H1 and H4 receptors ameliorates chronic allergic dermatitis via anti-pruritic and anti-inflammatory effects in NC/Nga mice", Allergy, vol. 67, No. 8, pp. 1014-1022, (2012).
Oksaharju, A. et al., "Probiotic lactobacillus rhamnosus downregulates FCER1 and HRH4 expression in human mast cells", World Journal of Gastroenterology, vol. 17, No. 6, pp. 750-759, (2011).
Paul, E. et al., "Effect of terfenadine and ranitidine on histamine and suxamethonium wheals", European Journal of Clinical Pharmacology, vol. 34, issue 6, pp. 591-594, (1988).
Poli, E. et al., "Functional characterisation of the novel histamine $H_3$ receptor agonist, VUF 5810, on the guinea-pig isolated ileum", Inflammation Research, vol. 53, supplemental 1, pp. S77-S78, (2004).
Reher, T.M. et al., "Incomplete activation of human eosinophils via the histamine $H_4$-receptor: evidence for ligand-specific receptor conformations", Biochemical Pharmacology, vol. 84, issue 2, pp. 192-203, (2012).
Rosenwasser, L.J. et al., "Mast cell stabilization and anti-histamine effects of olopatadine ophthalmic solution: a review of pre-clinical and clinical research", Current Medical Research & Opinion, vol. 21, No. 9, pp. 1377-1387, (2005).
Sander, L.E. et al., "Selective expression of histamine receptors H1R, H2R, and H4R, but not H3R, in the human intestinal tract", Gut, vol. 55, pp. 498-504, (2006).
Simons, F. et al., "Effect of the $H_2$-antagonist cimetidine on the pharmacokinetics and pharmacodynamics of the $H_1$-antagonists hydroxyzine and cetirizine in patients with chronic urticaria", Journal of Allergy and Clinical Immunology, vol. 95, issue 3, pp. 685-693, (1995).
Stokes, J.R. et al., "The effects of an $H_3$ receptor antagonist (PF-03654746) with fexofenadine on reducing allergic rhinitis symptoms", Journal of Allergy and Clinical Immunology, vol. 129, No. 2, pp. 409-412e2, (2012).
Takeshita, K. et al., "Critical role of L-selectin and histamine H4 receptor in zymosan-induced neutrophil recruitment from the bone marrow: comparison with carrageenan", The Journal of Pharmacology and Experimental Therapeutics, vol. 310, No. 1, pp. 272-280, (2004).
Varga, C. et al., "Inhibitory effects of histamine $H_4$ receptor antagonists on experimental colitis in the rat", European Journal of Pharmacology, vol. 522, issues 1-3, pp. 130-138, (2005).
Walker, M.M. et al., "The role of eosinophils and mast cells in intestinal functional disease", Current Gastroenterology Reports, vol. 13, issue 4, pp. 323-330, (2011).
Wood, J.D., "Histamine, mast cells, and the enteric nervous system in the irritable bowel syndrome, enteritis, and food allergies", Gut, vol. 55, No. 4, pp. 445-447, (2006).
Breunig, E. et al., "Histamine excites neurones in the human submucous plexus through activation of H1, H2, H3 and H4 receptors", The Journal of Physiology, vol. 583, pt. 2, pp. 731-742, (2007).
Rijnierse, A. et al., "Mast cells and nerves tickle in the tummy: Implications for inflammatory bowel disease and irritable bowel syndrome", Pharmacology & Therapeutics, vol. 116, issue 2, pp. 207-235, (2007).
Fasano, A., "Zonulin and its regulation of intestinal barrier function: The biological door to inflammation, autoimmunity, and cancer", Physiological Reviews, vol. 91, pp. 151-175, (2011).
Fedorowicz, Z. et al., "Histamine H2-receptor antagonists for urticaria (review)", Cochrane Database of Systematic Reviews, Issue 3, pp. 1-35, (2012).
De Ponti, F., "Drug development for the irritable bowel syndrome: current challenges and future perspectives", Frontiers in Pharmacology, vol. 4, article 7, pp. 1-12, (2013).
Wald, A. et al., "Pathophysiology of irritable bowel syndrome", UpToDate, 13 pages, Mar. 2016.
Friedling, T. et al., "Diabetic autonomic neuropathy of the gastrointestinal tract", UpToDate, 13 pages, Mar. 2016.
Krishnamurthi, S.S., "Enterotoxicity of chemotherapeutic agents", UpToDate, 15 pages, Mar. 2016.
Riddle, M.S. et al., "ACG Clinical guideline: diagnosis, treatment, and prevention of acute diarrheal infections in adults", The American Journal of Gastroenterology, pp. 1-21, published online Apr. 12, 2016.
Guarino, B., "Abuse of diarrhea medicine you know well is alarming physicians", The Washington Post, Morning Mix, 3 pages, found at www.washingtonpost.com/news/morning-mix/wp/2016/05/04/physicians-alarmed-by-abuse-of-over-the-counter-diarrhea-medicine-you-know-well/, May 4, 2016.
Kushnir-Sukhov, N.M. et al., "Mastocytosis", Allergy and Allergic Disease, $2^{nd}$ edition, chapter 91, pp. 1878-1893, (2008).
Ishikawa, M. et al., "Drug interaction effects on antitumor drugs. XIII. Amelioration of cisplatin lethality and renal toxicity by chlorpromazine in mice", Biological & Pharmaceutical Bulletin, vol. 16, No. 11, pp. 1104-1107, (1993).
Coupet, J. et al., "Brain histamine H1- and H2-receptors and histamine-sensitive adenylate cyclase: effects of antipsychotics and antidepressants", European Journal of Pharmacology, vol. 74, pp. 149-155, (1981).
European Search Report dated Oct. 31, 2016, for EP application No. 14 722 445.5-1466, 5 pages.
Roch-Arveiller, M. et al., "In vitro effect of cetirizine on $PGE_2$ release by rat peritoneal macrophages and human monocytes", Agents and Actions, vol. 43, pp. 13-16, (1994).
Ahrens, R. et al., "Histamine-induced chloride secretion is mediated via $H_2$-receptors in the pig proximal colon", Inflammation Research, vol. 52, issue 2, pp. 79-85, (2003).
Zhang, L. et al., "Mast cells and irritable bowel syndrome: From the bench to the bedside", Journal of Neurogastroenterology and Motility, vol. 22, No. 2, pp. 181-192, (2016).
Liu, H. et al., "Effects of first and second generation antihistamines on muscarinic induced mucus gland cell ion transport" BMC Pharmacology, vol. 5, No. 8, pp. 1-10, (2005).
Deiteren, A. et al., "Histamine H4 and H1 receptors contribute to postinflammatory visceral hypersensitivity", Gut, vol. 63, No. 12, pp. 1873-1882, (2014).
"Guidance for Industry: Estimating the Maximum Safe Starting Dose in Initial Clinical Trials for Therapeutics in Adult Healthy

(56) References Cited

OTHER PUBLICATIONS

Volunteers", U.S. Department of Health and Human Services, Food and Drug Administration, Center for Drug Evaluation and Research (CDER), Pharmacology and Toxicology, 30 pages, (2005).
Barnes, C.L. et al., "Cetirizine: A new, nonsedating antihistamine", The Annals of Pharmacotherapy, vol. 27, pp. 464-470, (1993).
"$H_2$ antagonist" found at http://en.wikipedia.org/wiki/H2_antagonist, 4 pages, (2017).
Ghadir, M.R. et al., "Doxepin is more effective than nortriptyline and placebo for the treatment of diarrhea-predominant irritable bowel syndrome: A randomized triple-blind placebo-controlled trial", Tehran University Medical Journal, pp. 352-358, (2011). (with English Abstract).
"Nortriptyline" found at http://en.wikipedia.org/wiki/Nortriptyline, 10 pages, (2017).
"Search results for doxepin hydrochloride", Drugs & Biologies, 1 page, (2017).
Editorial Team, "What is IBS? New rome IV diagnostic criteria for IBS", IrritableBowelSyndrome.net, found at https://irritablebowelsyndrome.net/clinical/new-rome-iv-diagnostic-criteria/, pp. 1-4, printed on Dec. 21, 2017.
International Search Report and Written Opinion dated Mar. 12, 2018, for PCT application No. PCT/US2017/068355, 14 pages.
Stein, A. et al., "Chemotherapy-induced diarrhea: pathophysiology frequency and guideline-based management", Therapeutic Advances in Medical Oncology, vol. 2, No. 1, pp. 51-63, (2010).
Kharkevitch, D.A., Pharmacology, Gaeotar-media, pp. 371-377, (2008), with Statement of Relevance, 2 pages.
Sainsbury, A. et al., "Treatment of irritable bowel syndrome: beyond fiber and antispasmodic agents", Therapeutic Advances in Gastroenterology, vol. 4, No. 2, pp. 115-127, (2011).
U.S. Appl. No. 17/333,525, filed May 28, 2021.
Dhanya, N.B. et al., "Histamine 2 blocker potentiates the effects of histamine 1 blocker in suppressing histamine-induced wheal", Indian Journal Dermatol Venereol Leprol, vol. 74, No. 5, pp. 475-477, (2008).
Feb. 11, 2021, U.S. Appl. No. 16/513,342, U.S.
Mar. 4, 2021, U.S. Appl. No. 16/029,38, U.S.
May 18, 2021, U.S. Appl. No. 16/513,342, U.S.
Mar. 15, 2021, Application No. 273377, IL.
Apr. 22, 2021, Application No. 10-2021-7004881, KR.
Jun. 11, 2021, U.S. Appl. No. 16/029,384, U.S.
Jul. 13, 2021, U.S. Pat. No. 2,906,005, CA.
Nov. 1, 2021, U.S. Appl. No. 16/513,342, U.S.
Nov. 1, 2021, Application No. 2020-184294, JP.
Nov. 16, 2021, Application No. 19128600.4, KR.
Jan. 21, 2022, U.S. Appl. No. 16/513,342, U.S.
Feb. 23, 2022, Application No. 10-2021-7004881, KR.

\* cited by examiner

LOW DOSE PRODUCT AND METHOD FOR TREATING DIARRHEA

BACKGROUND

Diarrhea is a common condition characterized by increased frequency or fluidity of bowel movements. Diarrhea may cause dehydration and electrolyte abnormalities that may require hospitalization to replace lost fluids and electrolytes until the symptoms subside. Persistent, uncontrolled diarrhea can cause such severe malnutrition, electrolyte imbalances and dehydration that it may ultimately result in death. Acute diarrhea is usually treated with fluid and electrolyte replacement, dietary modifications and antidiarrheal or antimicrobial agents. Acute diarrhea complications may cause severe illness, especially in high-risk groups, for example patients with underlying immunosuppression or advanced age. Antidiarrheal treatment is also required in patients with chronic diarrhea. Empiric therapies routinely used for chronic diarrhea include: stool-modifying agents (such as psyllium and fiber), anticholinergic agents, opiates, antibiotics, and probiotics.

Chronic diarrhea may be a symptom of a chronic disease, for example irritable bowel syndrome (IBS). It has been estimated that the prevalence of chronic diarrhea in the United States is approximately 5%. IBS alone is estimated to affect 15-20% of the U.S. population, and accounts for at least 30% of all gastroenterology health care costs. In many cases, the cause of the chronic diarrhea is not found, the diagnosis remains uncertain, and empiric treatments unsuccessful. Thus, there is an ongoing need for antidiarrheal agents that effectively stop or greatly reduce bowel movements and fluid loss in patients undergoing treatment, to remove the cause of diarrhea, or in patients in which the cause of diarrhea is not found.

While the various forms of chronic diarrhea likely have different underlying mechanisms, common mechanisms are shared. For example, Intestinal tissues from patients with IBS-D have demonstrated increased epithelial gaps (tight junctions) that allow noxious stimuli/antigen exposure to activate the histamine pathways (Martinez C. et al., "The Jejunum of Diarrhea-Predominant Irritable Bowel Syndrome Shows Molecular Alterations in the Tight Junction Signaling Pathway That Are Associated With Mucosal Pathobiology and Clinical Manifestations" *Am J Gastroenterol* (2012) 107:736-746). Subsets of patients with chronic diarrhea, namely food allergy diarrhea and IBS-D, have elevated levels of H1 and H2 receptors (Sander, L. E. et al., "Selective Expression of Histamine Receptors H1R, H2R, and H4R, but Not H3R, in the Human Intestinal Tract." *Gut* 55.4 (2006): 498-504. *PMC*. Web. 5 Dec. 2016). The role of mast cell activation and histamine release has been well studied. Known effects of histamine release include decreased barrier integrity, increased vascular permeability, increased smooth muscle contraction, increased peristalsis, and pain. All of these effects can contribute to or be associated with chronic diarrhea patients (Zhang et al., "Mast Cells and Irritable Bowel Syndrome: From the Bench to the Bedside" J Neurogastroenterol Motil. 2016 Apr. 30; 22(2):181-92).

H1 and H2 receptor antagonists are two classes of antihistamines. H1 receptor antagonists are used in the symptomatic treatment of multiple conditions, including allergic rhinoconjunctivitis, relief of pruritus in patients with urticaria, and in patients with chronic asthma. Newer H1 receptor antagonists, such as cetirizine, are referred to as second-generation H1 receptor antagonists, and are more selective for peripheral H1 receptors than first-generation H1 receptor antagonists, which antagonize both the central and peripheral nervous system H1 receptors as well as cholinergic receptors. The selectivity significantly reduces the occurrence of adverse drug reactions, such as sedation, while still providing effective relief of allergic conditions.

H2 receptor antagonists, such as famotidine, are used primarily to treat symptoms of acid reflux, or gastroesophageal reflux disease. H2 receptor antagonists reduce the production of stomach acid. Often diarrhea is listed as a major side effect of H2 receptor antagonists.

It had previously been discovered that an H1 receptor antagonist and an H2 receptor antagonist, in combination, succeeded in treating diarrhea of various types. The combination of 10 mg of cetirizine and 20 mg of famotidine, administered to patients with diarrhea, resulted in 85-90% positive responders (See table I below). A positive responder is identified as having a 50% or more reduction in the number of stools per day or a change in stool formation from liquid to solid. No adverse reactions or events were reported. A control group was treated with standard doses of fiber (Metamucyl®) and an anticholinergic (Bentyl®); positive responders in the control group were less than 25%. See U.S. Pat. Pub., Pub. No. US2014/0275116.

TABLE 1

Study results

| Treatment Group | Number of Participants | Positive Responders | Non-Responders | Percent Responding |
| --- | --- | --- | --- | --- |
| famotidine and cetirizine | 26 | 25 | 1 | 96% |
| dicylcomine and psyllium | 8 | 1 | 7 | 12.5% |

Positive responders = Appreciable decrease in # of stools per day
Non-responders = No appreciable decrease in # of stools per day

SUMMARY

In a first aspect, the present invention is a method of treating diarrhea in a patient, comprising administering 2.0-7.0 mg of cetirizine and 3.0-15.0 mg of famotidine to a patient.

In a second aspect, the present invention is a method of treating diarrhea in a patient comprising administering 2.0-7.0 mg of cetirizine and 3.0-15.0 mg of famotidine to a patient. The cetirizine and famotidine are administered simultaneously.

In a third aspect, the present invention is a method of treating diarrhea in a patient, comprising administering 2.0-7.0 mg of cetirizine and 3.0-15.0 mg of famotidine to a patient. The patient has acute diarrhea, chronic diarrhea or IBS-D.

In a fourth aspect, the present invention is a method of treating diarrhea in a patient comprising administering 2.0-7.0 mg of cetirizine and 3.0-15.0 mg of famotidine to a patient. The patient does not have mastocytic enterocolitis.

In a fifth aspect, the present invention is a pharmaceutical composition for treating diarrhea, comprising 2.0-7.0 mg cetirizine and 3.0-15.0 mg famotidine.

In a sixth aspect, the present invention is a pharmaceutical composition for treating diarrhea, comprising 2.0-7.0 mg cetirizine and 3.0-15.0 mg famotidine. The pharmaceutical composition comprises a unit dosage form or a plurality of unit dosage forms.

Definitions

The term "diarrhea," means increased fluidity or frequency of stools.

The term "acute diarrhea" is ongoing diarrhea which has occurred for at most 4 weeks.

The term "chronic diarrhea" is ongoing diarrhea for more than 4 weeks.

The term "unit dosage form," means a single pre-measured dose, and includes tablets, pills, capsules, packets, suspensions, transdermal patches, and rectal suppositories.

DETAILED DESCRIPTION

Figure 1:
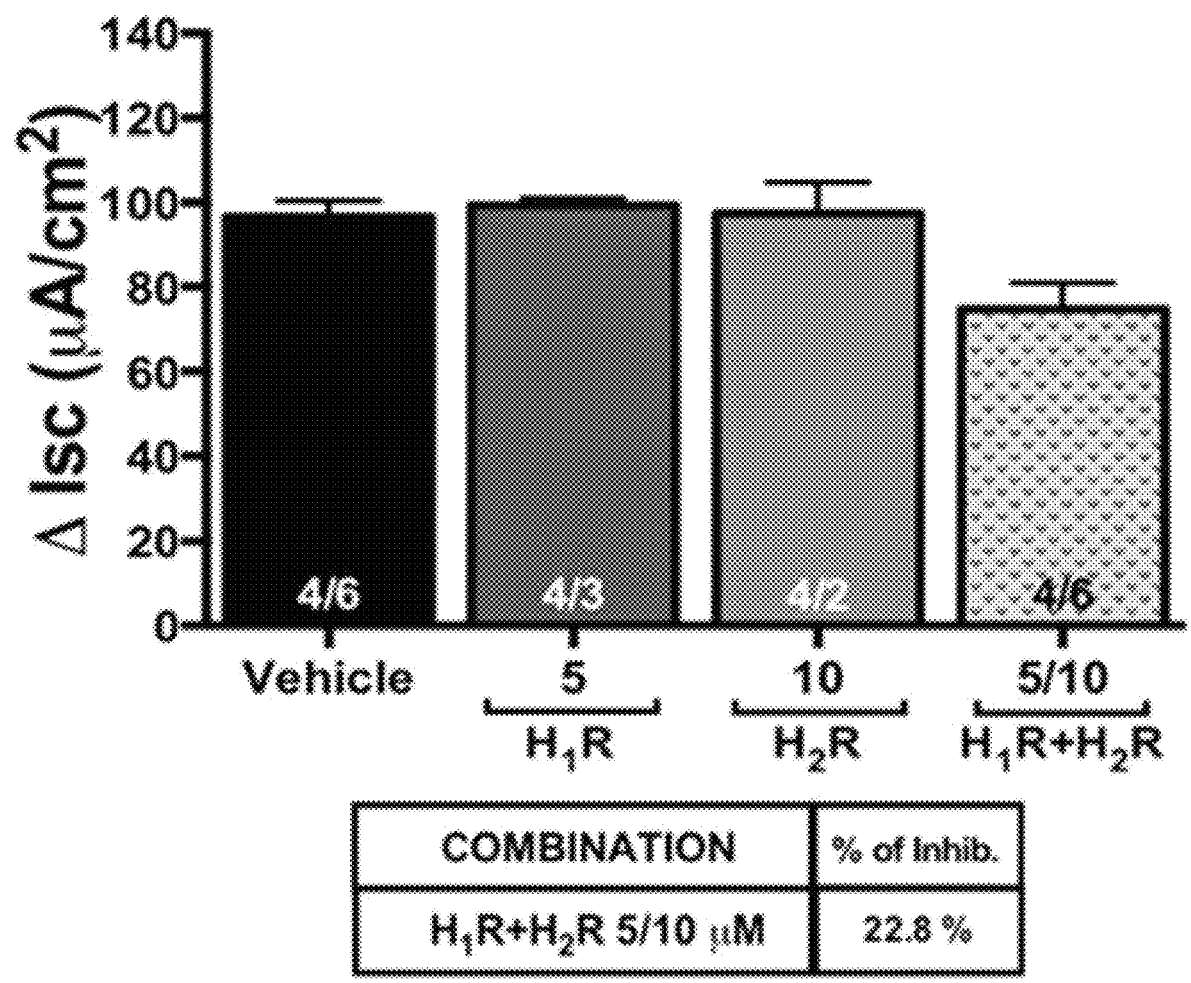
FIG. 1 is a chart showing the change in short-circuit current ($\Delta I_{SC}$) in rat colonic mucosa in the presence of vehicle alone, cetirizine alone, famotidine alone or cetirizine and famotidine in combination, where secretion was induced by electric field stimulation.

The present invention makes use of administering low doses of cetirizine and famotidine for treating diarrhea. The doses are lower than the typical doses of these drugs individually for treating allergies and acid reflux, respectively, and lower than doses of the two drugs combined previously for treating diarrhea. The synergistic effect of the two drugs allows for lower effective dosages than would otherwise be expected based on previous studies.

The present invention includes treating diarrhea by administering cetirizine and famotidine in combination. A series of in vitro tissue and in vivo animal experiments were performed to investigate the mechanism by which combination therapy of famotidine and cetirizine promotes clinical relief from severe diarrhea and visceral pain. The data from these experiments show that famotidine and cetirizine, in combination, were effective in three rat models of colonic hypersensitivity. At concentrations of 0.25 mg/kg and 0.6 mg/kg of cetirizine and famotidine, respectively, administered two times per day p.o., an increased inhibitory effect on colonic hypersensitivity was observed in all three models. The effective dosages, converted to human equivalent doses, are lower than the typical doses of these drugs individually. Testing of cetirizine and famotidine individually did not result in sufficient inhibition of colonic hypersensitivity in any of the three rat models.

Diarrhea may be acute or chronic. Diarrhea may also be further classified:

Secretory diarrhea: diarrhea which occurs when the intestine does not complete absorption of water from luminal contents and electrolyte absorption is impaired, often caused by bacterial toxins, surgically reduced absorptive area of the intestines, microscopic colitis and luminal secretagogues such as laxatives and bile acids.

Osmotic diarrhea: diarrhea that results from intestinal malabsorption of ingested non-electrolytes.

Inflammatory diarrhea: diarrhea which may be characterized by blood and pus in the stool and possibly an elevated fecal calprotectin level, and inflammation exhibited on intestinal biopsy, caused by, for example, Crohn's disease and ulcerative colitis.

IBS-diarrhea predominate ("IBS-D"): chronic diarrhea associated with abdominal pain. In order to have IBS, a patient must have experienced onset of symptoms 6 months prior to diagnosis and must have recurrent abdominal pain or discomfort at least one day per week in the last three months associated with two or more of the following: improvement with defecation; onset associated with a change in frequency of stool; onset associated with a change in form of stool. Once IBS is diagnosed, it can be further classified based on the patient's predominant symptom: diarrhea (IBS-D), or constipation (IBS-C), or mixed (IBS-M).

Functional diarrhea: chronic diarrhea in a patient who does not meet the criteria for IBS, and for which no other cause can be determined. This type of diarrhea may also be referred to as chronic idiopathic diarrhea.

Malabsorbtive diarrhea: diarrhea caused by an enteropathy such as celiac disease (celiac sprue) and giardiasis, which is characterized by excess gas, steatorrhea, and/or weight loss.

Drug induced diarrhea: diarrhea caused by a drug or treatment for an unrelated disease state, such as chemotherapy, radiation therapy, antibiotic therapy, anti-ulcer therapy, and herbal therapies.

Food intolerance diarrhea: diarrhea that is associated with dietary intake, such as lactose, sugar substitutes or other food substances.

Particularly common is IBS associated diarrhea, a chronic diarrhea, also referred to IBS-diarrhea predominate or simply "IBS-D". Some researchers claimed to have identified a subset of IBS-D, mastocytic enterocolitis, which they defined as a patient having greater than 20 mast cells per high-power field, based on an average of 10 high-power fields, for at least 2 separate biopsy pieces from random parts of the intestinal mucosa, using an original magnification of ×400, an objective having magnification of ×40 and an eyepiece having magnification of ×10 (Jakate, et al., "Mastocytic Enterocolitis: Increased mucosal mast cells in chronic intractable diarrhea" Arch Pathol Lab Med (2006) 130:362-367). In an aspect of the present invention, the patient does not have mastocytic enterocolitis.

The effective doses used in the three rat models of colonic hypersensitivity were converted to human effective doses using the FDA Guidance for Industry information. "Guidance for Industry: Estimating the Maximum Safe Starting Dose in Initial Clinical Trials for Therapeutics in Adult Healthy Volunteers" (July 2005) by U.S. Department of Health and Human Services, Food and Drug Administration, Center for Drug Evaluation and Research CDER. For example, doses of 0.25 mg/kg of cetirizine and 0.6 mg/kg of famotidine are doubled because the doses are administered twice a day. Then FDA guidelines are used to translate the doses to human equivalent doses of 4.82 mg of cetirizine and 11.6 mg of famotidine.

The cetirizine may be used in an amount of 2.0 to 7.0 mg per dose, including 2.0, 2.5, 3.0, 3.5, 4.0, 4.5, 5.0, 5.5, 6.0, 6.5 and 7.0 mg per dose. Preferably, the cetirizine is administered 1, 2, 3 or 4 times per day. The cetirizine may be administered as an injectable formulation, for example intravenously, intraparenterally or intramuscularly; transdermally, via a transdermal patch; or, preferably, orally, as a powder, tablet or capsule, an oral solution or suspension, or sublingual or buccal tablets. Alternative forms of administration include rectal suppositories, inhaled, epidural, subcutaneous, nasal spray, transmucosal, and intradermal formulations.

The famotidine may be used in an amount of 3.0 to 15.0 mg per dose, including 3.0, 3.5, 4.0, 4.5, 5.0, 5.5, 6.0, 6.5, 7.0, 7.5, 8.0, 8.5, 9.0, 9.5 10.0, 10.5, 11.0, 11.5, 12.0, 12.5, 13.0, 13.5, 14.0, 14.5 and 15.0 mg per dose. Preferably, the famotidine is administered 1, 2, 3 or 4 times per day. The famotidine may be administered as an injectable formulation, for example intravenously, intraparenterally or intramuscularly; transdermally, via a transdermal patch; or, preferably, orally, as a powder, tablet or capsule, an oral solution or suspension, or sublingual or buccal tablets. Alternative forms of administration include rectal suppositories, inhaled, epidural, subcutaneous, nasal spray, transmucosal, and intradermal formulations.

Patients often respond to treatment within 48 to 72 hours. However, treatment should be carried out for an amount of time to resolve any underlying cause in the case of acute diarrhea, for example 3 to 14 days, or 5 to 10 days. In the case of chronic diarrhea, a 30 day trial is reasonable, and if the underlying cause of the diarrhea cannot be resolved, for example in the case of IBS-D, then treatment should be continued indefinitely.

Preferably, the cetirizine and famotidine are administered simultaneously, as a unit dosage form containing both receptor antagonists. Examples of unit dosage forms include oral compositions, such as tablets (for example, oral, sublingual or buccal tablets), capsules (for example, hard gelatin and soft gelatin capsules), transmucosal and sublingual patches and films, pre-measured powder packets and saches, flavored and/or sweetened aqueous solutions or suspensions. Because diarrhea is often associated with dehydration, flavored and/or sweetened aqueous solutions or suspension may be oral rehydration solutions, or solutions which also contain sodium and glucose or a glucose-containing saccharide, in amounts of 250 ml, 500 ml or 1 liter of fluid. Furthermore, a pre-measured powder packet, containing the receptor antagonists, together with sodium (for example, as sodium chloride) and glucose or a glucose-containing saccharide, and optionally other excipients, flavorings and/or sweeteners, may be provided, which may be readily mixed with water prior to consumption. Preferably, the oral unit dosage form is present as a once-per-day dosage.

Examples of oral dosage forms include a tablet containing famotidine, in an amount of 3.0, 5.0, 7.5, 10.0, 12.5 or 15.0 mg, as a core, and a coating of cetirizine, in an amount of 2.0, 3.0, 4.0, 5.0, 6.0 or 7.0 mg. Another example includes a capsule containing granules of famotidine and cetirizine in water-soluble matrix. In another example, both the famotidine and the cetirizine are present as a mixture in a matrix, either as a tablet or within a capsule.

Other unit dosage forms may also be provided, containing both cetirizine and famotidine. For example, injectable formulation containing a sterile solution or suspension, including formulation for administration intravenously, intraparenterally or intramuscularly, may be provided. A unit dosage form for administration transdermally, via a transdermal patch, may be provided. Other unit dosage forms include rectal suppositories, inhaled, epidural, subcutaneous, nasal spray, and intradermal formulations. Excipients and adjuvants maybe also be included in any of the unit dosage forms, both oral and non-oral.

Multi-dosage forms, such as kits, containing 2 to 30, 3 to 25, or 5 to 14 unit dosage forms, for example 6, 7, 8, 9, 10, 11, 12, 13, 15, 20, 40, 50 or 60 unit dosage forms, may be provided. Preferably, the multi-dosage forms contain sufficient unit dosage forms for administration over a period of 2 to 30, 3 to 25, or 7 to 14 days, for example 4, 5, 6, 7, 8, 9, 10, 11, 12, 13, 20 or 30 days. Kits may also be provided, which include oral rehydration solutions, or powders which may be hydrated to form oral rehydration solutions, or kits containing sodium and glucose or a glucose-containing saccharide, as well as other excipients, flavorings and/or sweeteners, together with unit dosage forms.

Examples

In an effort to understand the potential efficacy of histamine H1 and H2 receptor antagonists to alleviate diarrhea, a series of in vitro and animal experiments were performed to investigate the mechanism by which combination therapy of famotidine and cetirizine promotes clinical relief from severe diarrhea and visceral pain.

In Vitro Experimental Results

The first experiment examined the effect of famotidine and cetirizine alone or in combination on nerve-mediated active electrolyte transport across the rat colonic mucosa in Ussing chambers. Active chloride secretion was induced by electrical field stimulation (EFS) at 16 Hz and the effects of famotidine and cetirizine individually and in combination on EFS-induced short circuit current ($I_{SC}$) were assessed under voltage-clamp conditions. Data are presented as mean±standard error of mean (SEM). Data were analyzed using 2-way analysis of variance employing Bonferroni's test for multiple comparisons. The famotidine and cetirizine concentration ranges evaluated were chosen based on previous published studies (Roch-Arveiller, M. et al., "In vitro effect of cetirizine on PGE 2 release by rat peritoneal macrophages and human monocytes" Agents and Actions (1994) 43:13; Liu, H. et al., "Effects of first and second generation antihistamines on muscarinic induced mucus gland cell ion transport" BMC Pharmacol. 2005 Mar. 24; 5:8; Ahrens, R. et al., "Histamine-induced chloride secretion is mediated via H2-receptors in the pig proximal colon" Inflammation Research (February 2003, Volume 52, Issue 2, pp 79-85); Deiteren et al., "Histamine H4 and H1 receptors contribute to postinflammatory visceral hypersensitivity" Gut. 2014 December; 63(12):1873-82).

FIG. 1 demonstrates that the combination of 10 µM famotidine and 5 µM cetirizine reduced electrical field stimulation-induced short-circuit current. Low concentrations of famotidine (10 µM) and cetirizine (5 µM) had no effect on EFS-induced $\Delta I_{SC}$ across the rat colonic mucosa when the agents were applied individually. However, the combination of famotdine (10 µM) and cetirizine (5 µM) significantly inhibited EFS-induced $\Delta I_{SC}$. In FIG. 1, "H1R" is cetirizine, "H2R" is famotidine and "Inhib" is inhibition.

Figure 2:
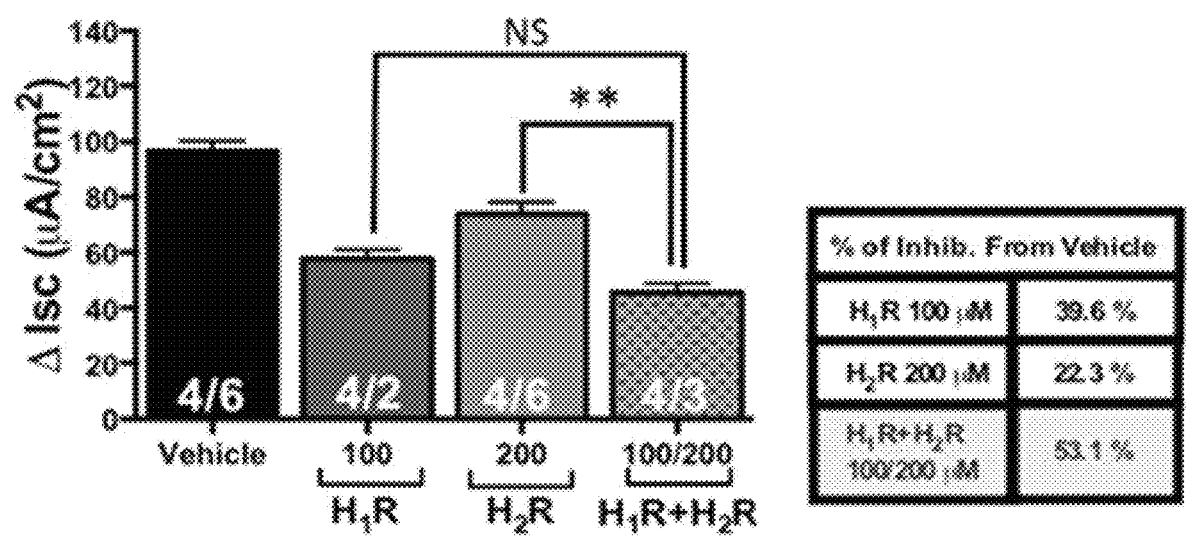
FIG. 2 is a chart showing the change in short-circuit current in rat colonic mucosa in the presence of vehicle alone, cetirizine alone, famotidine alone or cetirizine and famotidine in combination, where secretion was induced by electric field stimulation.

FIG. 2 shows that while modest changes in $I_{SC}$ were observed at very high concentrations of individual drugs (famotidine 200 µM, certirizine 100 µM), only the combination of famotidine (200 µM) and cetirizine (100 µM) produced a larger inhibition of the EFS-induced $\Delta I_{sc}$ than either compound alone at these concentrations.

These experiments demonstrated that the combination of famotidine and cetirizine significantly inhibited nerve-mediated ion transport across the rat colonic mucosa. Inhibition of ion transport would be expected to reduce the secretion of electrolytes and associated water thereby reducing the incidence and/or severity of diarrhea.

This first series of in vitro experiments demonstrated that combining doses of cetirizine and famotidine, while non-effective individually, attenuated active ion transport induced by neural stimulation, that is EFS. Additional in vitro studies were conducted to determine whether the combination of famotidine and cetirizine inhibited active ion secretion induced by prostaglandin $E_2$ ($PGE_2$) or forskolin. These secretogogues were selected because $PGE_2$ mediates the occurrence of watery diarrhea in response to a low-grade inflammatory insult and forakolin because it selectively activates all forms of cAMP-mediated intestinal secretion.

The in vitro experimental conditions were identical to those described previously except that electrical field stimulation was not used. Rather, $PGE_2$ (prostaglandin $E_2$) or forskolin was applied to the serosal side of the mucosal preparation to induce an increase in $I_{SC}$ as an electrophysiological indication of net active ion transport across the colonic mucosa. The increase in active ion transport was calculated as the difference between maximum $I_{SC}$ and baseline $I_{SC}$ divided by 0.6 (exposed tissue area in cm$^2$). Data are presented as mean±SEM. Data were analyzed using 1-way ANOVA followed by a Bonferroni post-test.

Figure 3:
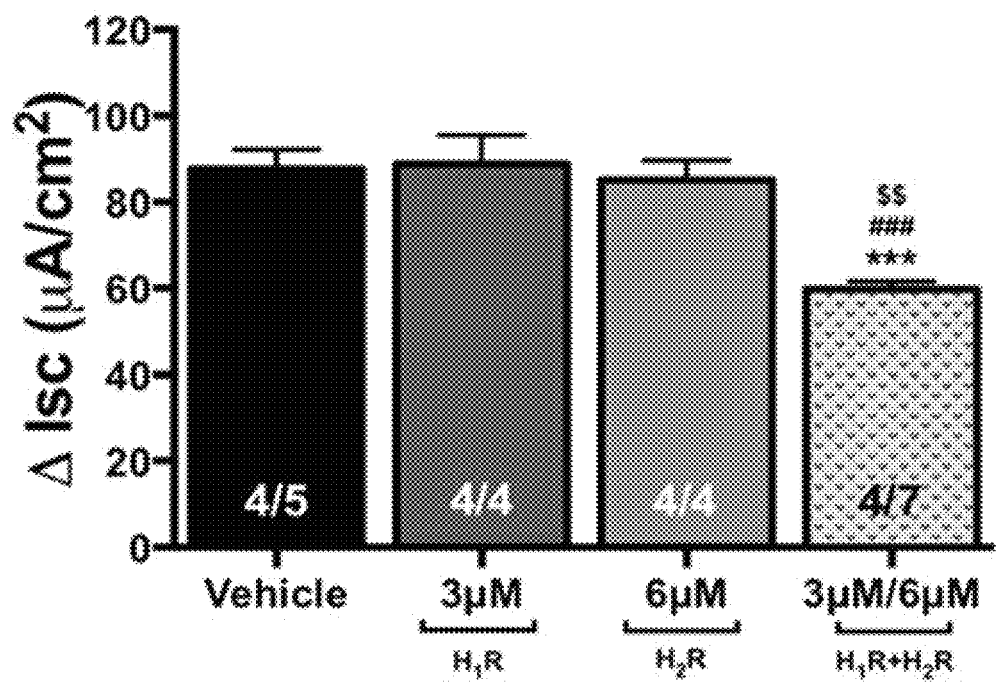
FIG. 3 is a chart showing the change in short-circuit current in rat colonic mucosa in the presence of vehicle alone, cetirizine alone, famotidine alone or cetirizine and famotidine in combination, where secretion was induced with $PGE_2$.

FIG. 3 demonstrates that at concentrations of 6 µM famotidine and 3 µM cetirizine, neither drug alone was effective; however, the combination of famotidine and cetirizine at these concentrations significantly inhibited (31.8%) $PGE_2$-induced changes in $I_{SC}$. The data showed statistical significance at levels of P<0.001 combination compared to vehicle, P<0.001 combination compared to 3 µM cetirizine and P<0.05 combination compared to 6 µM famotidine.

Figure 4:
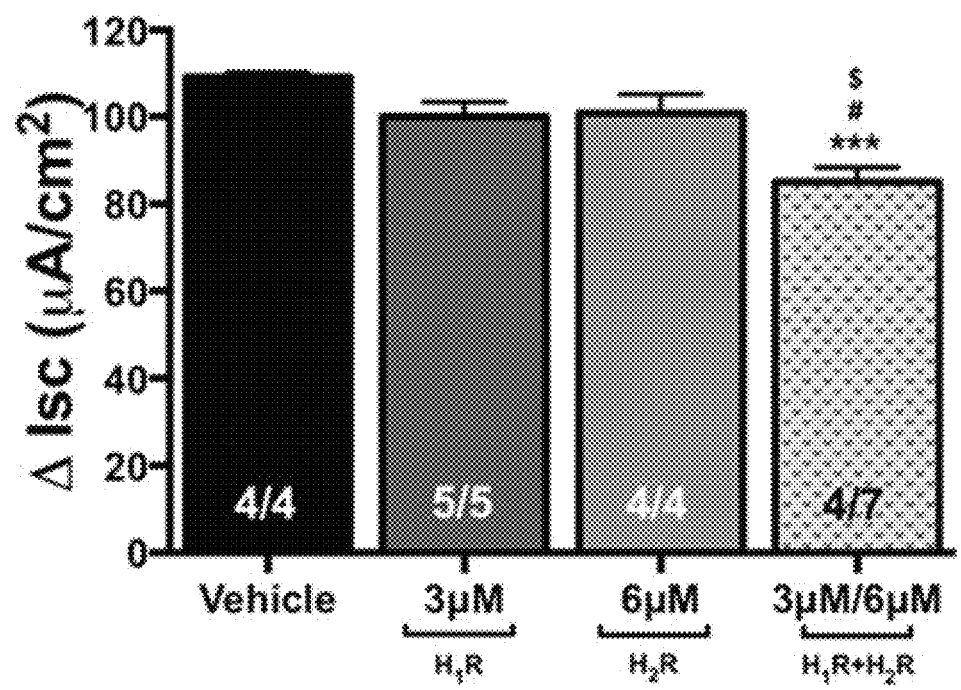
FIG. 4 is a chart showing the change in short-circuit current in rat colonic mucosa in the presence of vehicle alone, cetirizine alone, famotidine alone or cetirizine and famotidine in combination, where secretion was induced with forskolin.

Similar to the results observed for $PGE_2$ treatment, at concentrations of 6 µM famotidine and 3 µM cetirizine, each drug alone was only minimally effective in inhibiting forskolin-induced changes in $I_{SC}$. However, FIG. 4 shows the combination of 6 µM famotidine and 3 µM cetirizine significantly inhibited (22.0%) forskolin-induced changes in $I_{SC}$. The data showed statistical significant levels of P<0.001 combination compared to vehicle, P<0.5 combination compared to 3 µM cetirizine and P<0.05 combination compared to 6 µM famotidine.

Taken together, these data demonstrate that famotidine and cetirizine in combination attenuate $PGE_2$-induced and forskolin-induced changes in rat $I_{SC}$ across the isolated rat colonic mucosa; these results are consistent with those observed for electrical field stimulation of $I_{SC}$ as shown in FIG. 2.

In Vivo Experimental Results

The first in vivo study evaluated the efficacy of famotidine and cetirizine alone and in combination on visceral pain using chronic water avoidance stress (WAS), an experimental animal model of stress-induced visceral hypersensitivity. Male Fischer rats (250-300 g) were acclimated to the animal facility, laboratory, and animal handlers for 2 weeks before exposure to the chronic stressor. Rats were removed from their home cage and placed on a platform surrounded by water for 1 hour. This procedure was performed daily for 10 days. As a verification that the rats did not habituate to the daily stressor, fecal pellet output (FPO) was assessed during each WAS exposure to verify the effect of stress on autonomic outflow.

Twenty-four hours after exposure to the final day of WAS (day 10), a visceromotor behavioral response (VMR) to colorectal distension (CRD) was used to assess colonic sensitivity. VMR was quantified as the number of abdominal contractions in response to graded (0, 20, 40, and 60 mmHg) pressures of isobaric CRD that were administered in a randomized manner. Immediately following VMR to CRD, rats were euthanized and terminal blood was collected for potential PK analysis. Rats were dosed orally, twice daily, for 3.5 days with vehicle control or with cetirizine and famotidine alone or in combination. The final dose was administered 1 hour before the colonic sensitivity assessment. Data are presented as mean±SEM. Data were analyzed using 2-way analysis of variance followed by a Bonferroni's test for multiple comparisons. The famotidine and cetirizine concentration ranges examined were chosen based on previous published studies (Roch-Arveiller, M. et al., "In vitro effect of cetirizine on PGE 2 release by rat peritoneal macrophages and human monocytes" Agents and Actions (1994) 43:13; Liu, H. et al., "Effects of first and second generation antihistamines on muscarinic induced mucus gland cell ion transport" BMC Pharmacol. 2005 Mar. 24; 5:8; Ahrens, R. et al., "Histamine-induced chloride secretion is mediated via H2-receptors in the pig proximal colon" Inflammation Research (February 2003, Volume 52, Issue 2, pp 79-85); Deiteren et al., "Histamine H4 and H1 receptors contribute to postinflammatory visceral hypersensitivity" Gut. 2014 December; 63(12):1873-82).

Daily water avoidance stress consistently increased the number of fecal pellets. The administration of cetirizine and famotidine, alone or in combination, had no effects on fecal output and thus did not alter stress levels themselves to confound the data.

Figure 5:
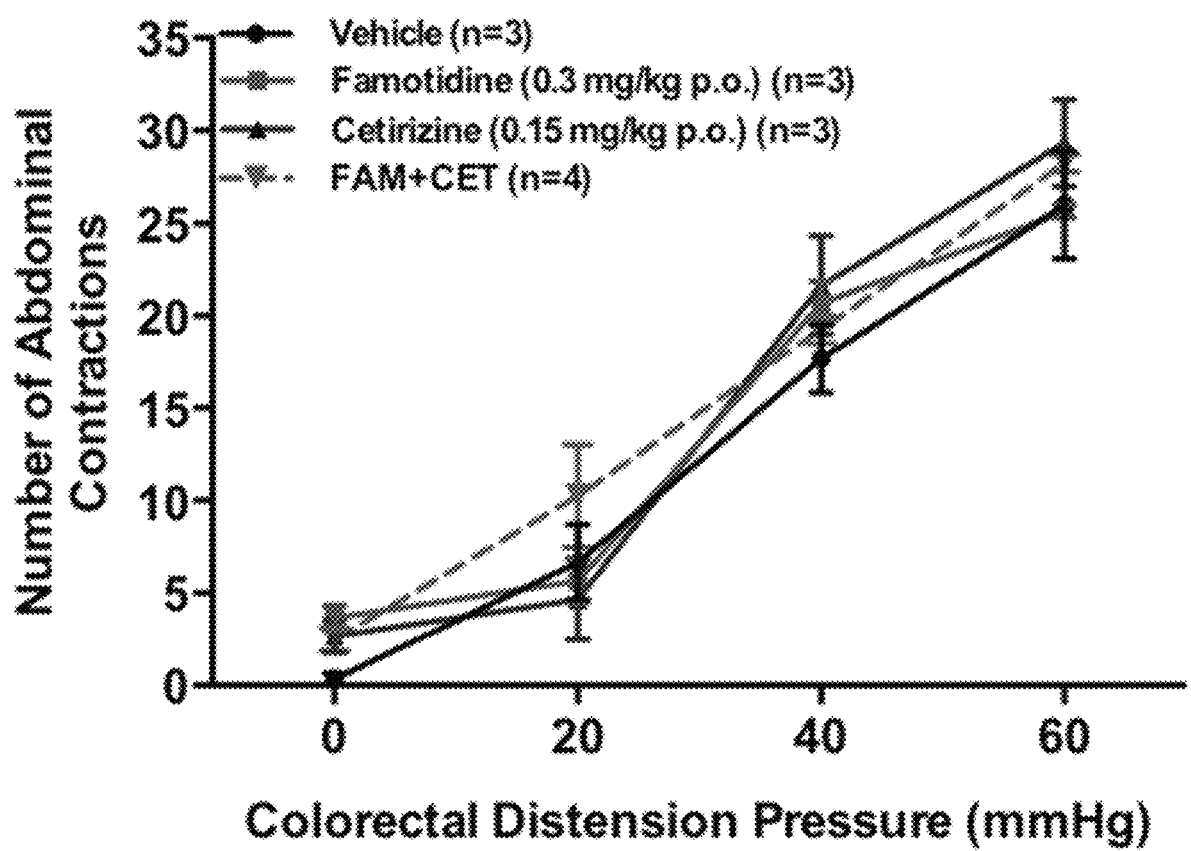
FIG. 5 is a chart showing the change in the number of abdominal contractions with colorectal distension pressure for rats receiving doses of vehicle alone, cetirizine alone (0.15 mg/kg), famotidine alone (0.3 mg/kg) or cetirizine and famotidine in combination in the water avoidance stress-induced colonic hypersensitivity model.

FIG. 5 shows that at the lowest tested doses, administration of famotidine (0.3 mg/kg) and cetirizine (0.15 mg/kg) alone or in combination had no effect on colonic hypersensitivity. In FIG. 5: Fam=famotidine; CET=cetirizine; n=number of animals.

Figure 6:
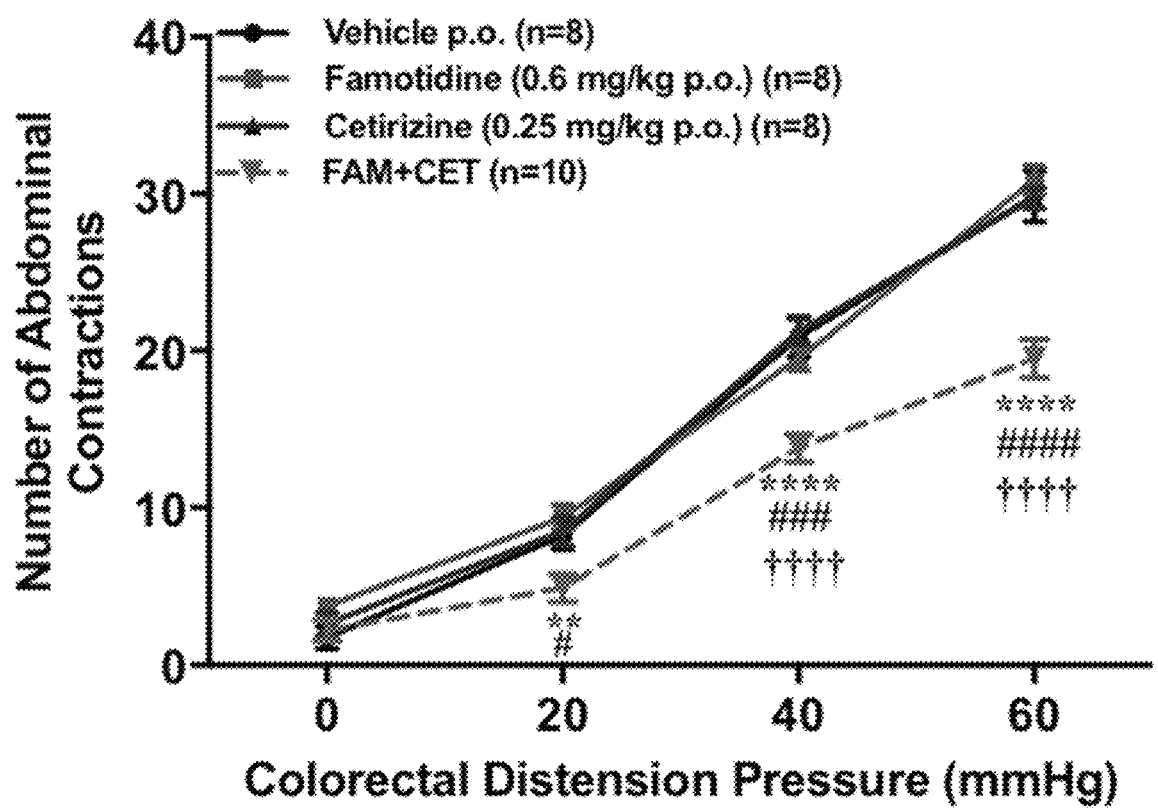
FIG. 6 is a chart showing the change in the number of abdominal contractions with colorectal distension pressure for rats receiving doses of vehicle alone, cetirizine alone (0.25 mg/kg), famotidine alone (0.6 mg/kg) or cetirizine and famotidine in combination in the water avoidance stress-induced colonic hypersensitivity model.

At a higher dose of the combination of famotidine (0.6 mg/kg) and cetirizine (0.25 mg/kg), an increased inhibitory effect on colonic hypersensitivity compared to either treatment alone was observed. FIG. 6 shows that, at these doses, neither drug alone had an effect, while the combination of famotidine and cetirizine increased the inhibitory effect by 19.2%. In FIG. 6: ††††=p<0.0001 for the combination compared to vehicle; =p<0.01 and **p<0.0001 for the combination compared to famotidine; and #=p<0.05 and ###=p<0.001 and ####=p<0.0001 for the combination compared to cetirizine.

Figure 7:
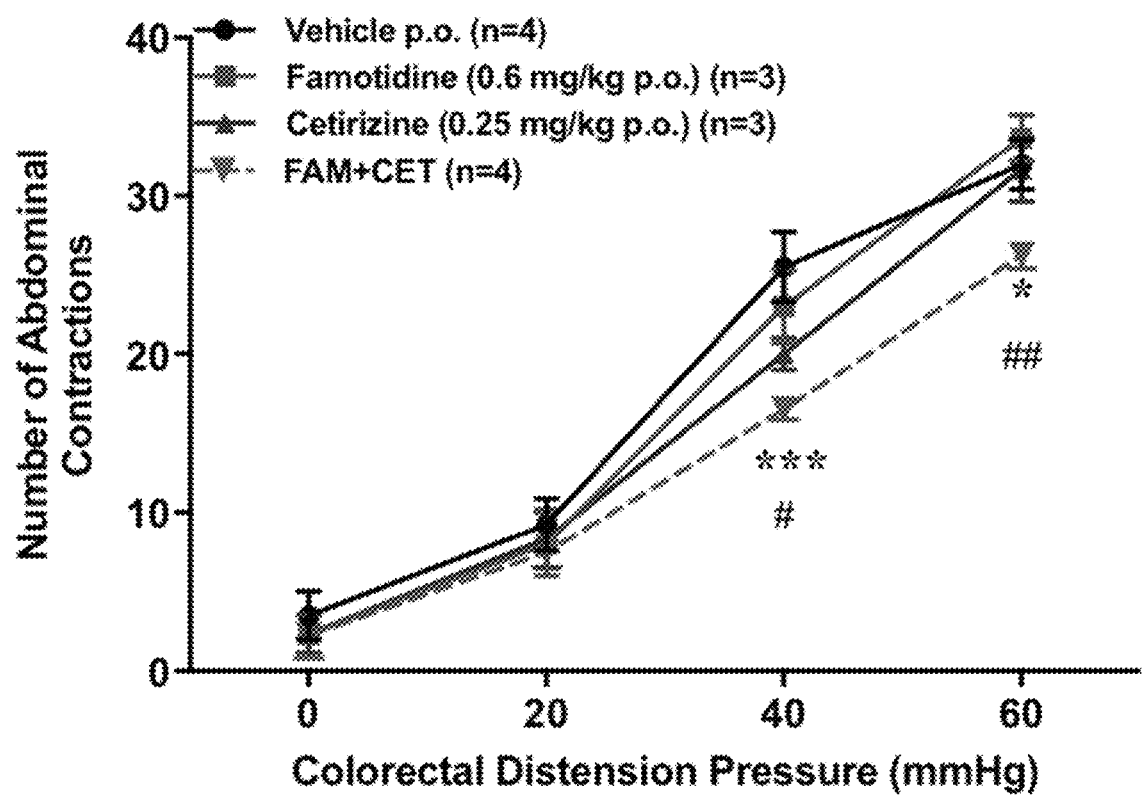
FIG. 7 is a chart showing the change in the number of abdominal contractions with colorectal distension pressure for rats receiving doses of vehicle alone, cetirizine alone, famotidine alone or cetirizine and famotidine in combination in the acetic acid-induced colonic hypersensitivity model.

In a second rodent model, dilute acetic acid was employed to simulate colonic irritation in order to examine the potential effects of famotidine and cetirizine. Male Sprague-Dawley rats (290-360 g) were acclimated to the animal facility for 2 weeks before being subjected to acute colonic sensitization. Rats were dosed orally with vehicle control, famotidine (0.6 mg/kg), cetirizine (0.25 mg/kg), or the combination of famotidine and cetirizine for 3.5 days, twice daily. The final dose was administered 1 hour before the colonic sensitivity assessment Dilute acetic acid (1.5 ml of 0.6% acetic acid) was infused into the mid-to-distal colon 1 hour prior to colonic sensitivity assessment. One hour following colonic infusion of acetic acid, a VMR to CRD was used to assess colonic sensitivity. The VMR was quantified as the number of abdominal contractions in response to graded (0, 20, 40, and 60 mg Hg) pressures of isobaric CRD that were administered in a randomized manner. Data were analyzed using 2-way ANOVA followed by a Bonferroni's test for multiple comparisons. FIG. 7 demonstrates that the combination of famotidine and cetirizine, but not either drug alone, induced a significant inhibition (26.7% inhibition at 40 mm Hg and 17.8% inhibition at 60 mmHg) of acetic acid-induced colonic hypersensitivity. In FIG. 7: *=$p<0.05$ and *** $p<0.001$ for the combination compared to vehicle; #=$p<0.05$ and ##=$p<0.001$ for the combination compared to famotidine In the third rodent model, 2,4,6-trinitrobenzenesulfonic acid (TNBS) was used to induce acute colitis in adult rats. Male Sprague-Dawley rats (260-310 g) acclimated to the animal facility for 2 weeks before being subjected to chronic sensitization. Following an overnight fast, an acute colitis was induced by daily intracolonic infusion of 0.5 mL of TNBS (50 mg/kg in 25% ethanol) for 7 days. TNBS-induced inflammation was assessed via Disease Activity Index (DAI) for each of the 7 days following TNBS infusion.

In the TNBS study, colonic hypersensitivity was assessed via VMR to CRD at day 15 post-TNBS. Rats were subjected to 3 colonic distensions at 40 mm Hg, and animals that demonstrated 18 or more abdominal contractions during any of the distension periods were designated as qualifiers and allowed to proceed in the study. Animals that demonstrated fewer than 18 abdominal contractions were designated as non-qualifiers and removed from the study. Final colonic hypersensitivity assessment was conducted on qualified animals between from 28 to 30 post-TNBS via VMR to CRD at graded distension pressures of 0, 20, 40, and 60 mm Hg administered in random fashion.

Rats were dosed orally with 0.25 mg/kg cetirizine or 0.6 mg/kg famotidine twice daily for 3.5 days or with cetirizine and famotidine in combination at the same dose and schedule. The final dose was administered 1 hour before the final colonic sensitivity assessment.

Figure 8:
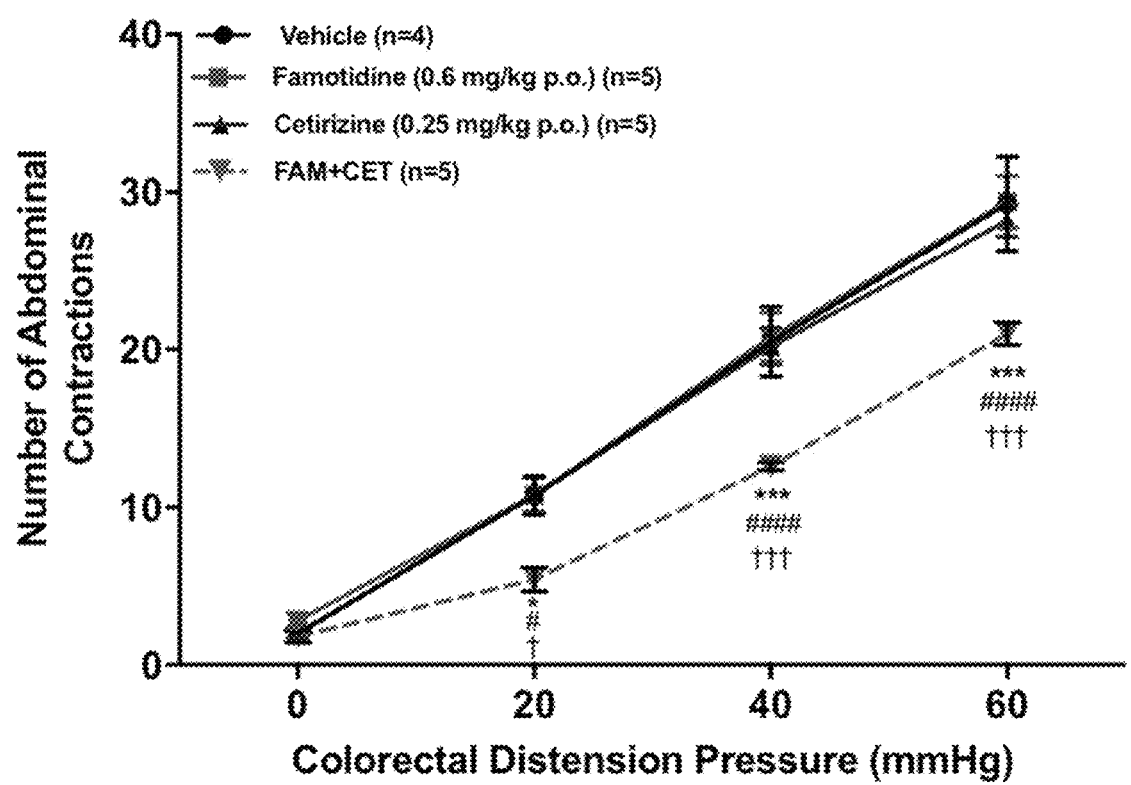
FIG. 8 is a chart showing change in the number of abdominal contractions with colorectal distension pressure for rats receiving doses of vehicle alone, cetirizine alone, famotidine alone or cetirizine and famotidine in combination in the TNBS-induced colonic hypersensitivity model.

Results shown in FIG. 8 demonstrate an effect on inhibition of TNBS-induced, post-inflammatory colonic hypersensitivity by the cetirizine and famotidine combination. Neither cetirizine alone nor famotidine alone exhibited any effect, but the combination of famotidine and cetirizine significantly decreased colonic hypersensitivity at 40 mm Hg CRD (38.5% inhibition) and 60 m Hg CRD (28.3% inhibition). In FIG. 8 *=$p<0.05$ and *=$p<0.001$ for the combination compared to vehicle; #=$p<0.05$ and ####=$p<0.001$ for the combination compared to famotidine; and †=$p<0.05$ and †††=$p<0.001$ for the combination compared to cetirizine.

The in vitro and in vivo data demonstrate that the combination of cetirizine and famotidine effectively attenuates colonic hypersensitivity in multiple rodent models of colonic hypersensitivity that resemble the IBS phenotype.

REFERENCES

Schiller L R, "Secretory Diarrhea" *Current Gastroenterology Reports* (1999) 1:389-397.

Schiller, L R, Hogan R B, Morawski, S G, Santa Ana, Calif., Bern M J, Nogaard, R P, Bo-Linn, G W, Fordtran J S, "Studies of the Prevalence and Significance of Radiolabeled Rice Acid Malabsorption in a Group of Patients with Idiopathic Chronic Diarrhea" *Gastroenterology* (1997) 92:151-160.

Fordtran J S, Santa Ana Calif., Morawski S G, et al. "Pathophysiology of chronic diarrhea: insights derived from intestinal perfusion studies in 31 patients" *Gastroenterol Clin North Am* (1986) 15:477-490.

Lunardi C, Bambara L M, Biasi D, et al. "Double-blind cross-over trial of oral sodium cromoglycate in patients with irritable bowel syndrome due to food intolerance" *Clin Exp Allergy* (1991) 21: 569-572.

Fine K D, Schiller U R, "AGA technical review on the evaluation and management of chronic diarrhea" *Gastroenterology* (1999) 116:1464-1486.

O'Sullivan et al. "Increased mast cells in the irritable bowel syndrome" *Neurogastroenterol. Mot.* (2000) 12:449-457.

Spiller R C, Jenkins D, Thornley J P, Hebden J M, Wright T, Skinner M, Neal K R, "Increased rectal mucosal enteroendocrine cells, T lymphocytes, and increased gut permeability following acute *Campylobacter* enteritis and in post-dysenteric irritable bowel syndrome" *Gut* (December 2000) 47(6):804-11.

Theoharides T C Cochrane D E, "Critical role of Mast Cells in inflammatory diseases and the effect of acute stress" *J Neuroimmunol* (2004) 146:1-12.

Barbars G, De Giorgio et al. "New pathophysiological mechanisms in irritable bowel syndrome" *Aliment Pharmacol Ther* (2004) 20(suppl. 2):1-9.

Dunlop S P, Hebden et al. "Abnormal intestinal permeability in subgroups of diarrhea-predominant irritable bowel syndromes" *Am J Gastroenterol* (2006) 101(6):1288-1294.

Barbara G, Stanghellini V et al. "Functional gastrointestinal disorders and mast cells: implications for therapy" *Neurogastroenterol Motil* (2006) 18:6-17.

Halvorson H A et al. "Postinfectious irritable bowel syndrome-a meta-analysis" *Am J Gastroenterol* (2006) 101: 1894-1899.

Posserud I et al. "Small intestinal bacterial overgrowth in patients with irritable bowel syndrome" *Gut* (2007) 56:802-808.

Lewis, J, Candelora, J, Hogan, I I, RB, Briggs, F, Abraham, S, "Crystal-Storing Histiocytosis Due to Massive Accumulation of Charcot-Leyden Crystals: A Unique Association Producing Colonic Polyposis in a 78-year-old Woman With Eosinophilic Colitis" *Am J Surg Pathol.* (March 2007) 321(3):481-485.

Jakate S, et al. "Mastocytic enterocolitis increased mucosal mast cells in chronic intractable diarrhea" *Arch Pathol Lab Med*, (2006) 130:362-367.

Kirsch R H, Riddell R, "Histopathological alterations in irritable bowel syndrome" *Modern Pathology* (2006) 19:1638-1645.

Ramos L, Vicario M, Santos J, "Stress-mast cell axis and regulation of gut mucosal inflammation: from intestinal health to an irritable bowel" *Med Clin (Barc)* (June 2007) 129(2):61-69.

Piche T, Saint-Paul M C et al. "Mast cells and cellularity of the colonic mucosa correlated with fatigue and depression in irritable bowel syndrome" *Gut* (2008) 57:468-473.

Visser J, Rozing et al. "Tight Junctions, intestinal permeability and autoimmunity celiac disease and type 1 diabetes paradigms" *Ann N Y Acad Sci* (2009) 1165:195-205.

Waker M M, Talley N J, et al. "Duodenal mastocytosis, eosinophilla and intraepithelial lymphocytosis as possible disease markers in the irritable bowel syndrome and functional dyspepsia" *Aliment Pharmacol Ther* (2009) 29:765-773.

Thabane M, Marshall J K, "Post-infectious irritable bowel syndrome" *World J Gastroenterol.* (2009) 15(29):3591-3596.

Walker M M, Salehian S S et al. "Implications of eosinophilia in the normal duodenal biopsy—an association with allergy and functional dyspepsia" *Aliment Pharmacol Ther* (2010) 31:1229-1236.

Klooker T K, Braak B, Koopman K E et al. "The mast cell stabilizer ketotifen decreases visceral hypersensitivity and improves intestinal symptoms in patients with irritable bowel syndrome" *Gut* (2010) 59:1213-21.

Martinez C, et al. "The Jejunum of Diarrhea-Predominant Irritable Bowel Syndrome Shows Molecular Alterations in the Tight Junction Signaling Pathway That Are Associated With Mucosal Pathobiology and Clinical Manifestations" *Am J Gastroenterol* (2012) 107:736-746.

Theoharides T C, Shahrzad A, Chen J, Huizinga J, "Irritable Bowel Syndrome and the Elusive Mast Cell" *Am J Gastroenterol* (2012) 107:727-729.

Smith M J, "IBS remains a mysterious disorder with few effective Remedies" *Gastroenterology and Endoscopy News* (April 2012) Vol. 63:4.

Pyleris E, Giamarellos-Bourboulis E J, et al. "The prevalence of overgrowth by aerobic bacteria in the small intestine by small bowel culture: relationship with irritable bowel syndrome" *Dig Dis Sci.* (May 2012) 57(5): 1321-9.

Vivinus-Nebot M, Dainese R, et al. "Combination of allergic factors can worsen diarrheic irritable bowel syndrome: role of barrier defects and mast cells" *ACG* (2012) 107: 74-81

Akhavein A, Patel N R, et al. "Allergic Mastocytic Gastroenteritis and colitis: and unexplained etiology in chronic abdominal pain and gastrointestinal dysmotility" *Gastroenter Research and Practice* (2012) 2012:950582.

Martinez C, Lobo B, et al. "Diarrhoea-predominant irritable bowel syndrome: an organic disorder with structural abnormalities in the jejunal epithelial barrier" *Gut* (2012) [Epub ahead of print 25 May 2012].

Braak B, Klooker T K et al. "Mucosal immune cell numbers and visceral sensitivity in patients with irritable bowel syndrome: is there any relationship?" *Am J Gastroenterol* (2012) 107:715-726.

Theoharides T C, Asadi S, Chen J, Huizinga J D, "Irritable bowel syndrome and the elusive mast cells" *Am J Gastroenterol* (2012) 107(5):727-729.

Farhadi A, Fields J Z, Keshavarzian A, "Mucosal mast cells are pivotal elements in inflammatory bowel disease that connect the dots: stress, intestinal hyperpermeability and inflammation" *World J Gastroenterol* (2007) 13(22): 3027-3030.

Juckett G, Trivedi R, "Evaluation of chronic diarrhea" *American Family Physician* [serial online]. Nov. 15, 2011; 84(10): 1119-1126.

*Diarrhea* [electronic resource]/*National Digestive Diseases Information Clearinghouse.* (2011). Bethesda, Md.: U.S. Dept. of Health and Human Services, National Institutes of Diabetes and Digestive and Kidney Diseases.

Forbes D, O'Loughlin E, Scott R, Gall D, "Laxative abuse and secretory diarrhoea" *Arch Dis Child* (1985) 60(1):58-60.

DuPont, H. L. et al., "Diarrhea", *National Digestive Diseases Information Clearinghouse*, January 2012.

Lever, D. D., et al., "Acute Diarrhea", *Center for Continuing Education publications: Disease Management Project*, Cleveland Clinic, Aug. 1, 2010.

H2 blockers, MedlinePlus®, U.S. National Library of Medicine, NIH, updated: Aug. 11, 2011.

Runge et al. "Histamine antagonists in the treatment of acute allergic reactions" *Ann Emerg Med* (March 1992) 21:237-242.

Lin et al. "Improved outcomes in patients with acute allergic syndromes who are treated with combined H1 and H2 antagonists" *Ann Emerg Med* (November 2000) 36:462-468.

He, Shuang; U, Feng; Zhou, Dan; Du, Junrong; Huang, Yuan, Drug development and Industrial pharmacy, (October 2012) 38(10)1280-1289.

Akin C, Valent P, Metcalfe D D "Mast cell activation syndrome: Proposed diagnostic criteria" *J Allergy Clin Immunol.* (2010) 126(6):1099-104.

Hamilton M J, Homick J L, Akin C, Castells M C, Greenberger N J "Mast cell activation syndrome: a newly recognized disorder with systemic clinical manifestations" *J Allergy Clin Immunol.* (2011) 128(1):147-152.

Valent P "Mast cell activation syndromes: definition and classification" *Allergy* (2013) [Epub ahead of print 15 Feb. 2013].

Sander, L. E. et al., "Selective Expression of Histamine Receptors H1R, H2R, and H4R, but Not H3R, in the Human Intestinal Tract." *Gut* 55.4 (2006): 498-504. *PMC.* Web. 5 Dec. 2016.

Roch-Arveiller, M. et al., "In vitro effect of cetirizine on PGE 2 release by rat peritoneal macrophages and human monocytes" *Agents and Actions* (1994) 43:13.

Ahrens, R. et al., "Histamine-induced chloride secretion is mediated via H2-receptors in the pig proximal colon" *Inflammation Research* (February 2003, Volume 52, Issue 2, pp 79-85).

Zhang et al., "Mast Cells and Irritable Bowel Syndrome: From the Bench to the Bedside" J Neurogastroenterol Motil. 2016 Apr. 30; 22(2):181-92.

Liu, H. et al., "Effects of first and second generation antihistamines on muscarinic induced mucus gland cell ion transport" BMC Pharmacol. 2005 Mar. 24; 5:8.

Delteren et al., "Histamine H4 and H1 receptors contribute to postinflammatory visceral hypersensitivity" Gut. 2014 December; 63(12):1873-82.

"Guidance for Industry: Estimating the Maximum Safe Starting Dose in Initial Clinical Trials for Therapeutics in Adult Healthy Volunteers" (July 2005) by U.S. Department of Health and Human Services, Food and Drug Administration, Center for Drug Evaluation and Research CDER.

What is claimed is:

1. A method of treating diarrhea in a patient, comprising: administering cetirizine and famotidine, wherein the cetirizine is administered in a dose of 6.0-7.0 mg per day and the famotidine is administered in a dose of 12.0-15.0 mg per day.

2. The method of claim 1, wherein the cetirizine is administered in a dose of 6.5-7.0 mg per day and the famotidine is administered in a dose of 14.0-15.0 mg per day.

3. The method of claim 1, wherein the patient has chronic diarrhea.

4. The method of claim 1, wherein the patient has acute diarrhea.

5. The method of claim 1, wherein the cetirizine and famotidine are administered simultaneously.

6. The method of claim 1, wherein cetirizine and famotidine are administered once per day for at least 2 days.

7. The method of claim 1, wherein the cetirizine and famotidine are administered once per day for at least 7 days.

8. The method of claim 1, wherein the patient does not have mastocytic enterocolitis.

9. A method of treating IBS-D in a patient, comprising: administering cetirizine and famotidine to the patient, wherein the cetirizine is administered in a dose of 6.0-7.0 mg per day and the famotidine is administered in a dose of 12.0-15.0 mg per day.

10. The method of claim 1, wherein the diarrhea is selected from the group consisting of: secretory diarrhea, osmotic diarrhea, inflammatory diarrhea, functional diarrhea, malabsorbtive diarrhea, drug induced diarrhea and food intolerance diarrhea.

11. The method of claim 9, wherein the cetirizine is administered in a dose of 6.5-7.0 mg per day and the famotidine is administered in a dose of 14.0-15.0 mg per day.

12. The method of claim 9, wherein the cetirizine and famotidine are administered simultaneously.

13. The method of claim 9, wherein cetirizine and famotidine are administered once per day for at least 2 days.

14. The method of claim 9, wherein the cetirizine and famotidine are administered once per day for at least 7 days.

15. The method of claim 9, wherein the patient does not have mastocytic enterocolitis.

\* \* \* \* \*